United States Patent [19]

Carron

[11] Patent Number: 5,693,152
[45] Date of Patent: Dec. 2, 1997

[54] MOLECULAR SPECIFIC DETECTOR FOR SEPARATION SCIENCE USING SURFACE ENHANCED RAMAN SPECTROSCOPY

[75] Inventor: Keith T. Carron, Laramie, Wyo.

[73] Assignee: University of Wyoming, Laramie, Wyo.

[21] Appl. No.: 514,667

[22] Filed: Aug. 14, 1995

[51] Int. Cl.$^6$ ............................ C23C 22/00; G01J 3/44; C23F 11/00
[52] U.S. Cl. ............ 148/271; 210/93; 210/94; 356/301; 422/7; 427/162; 252/395
[58] Field of Search ................. 210/94, 198.2, 210/656, 745; 422/7, 12, 13, 82.05, 82.08, 82.09; 356/300, 301, 326; 427/250, 307, 309, 327, 162, 163.2, 273, 280, 287, 337, 343; 148/240, 271; 436/164, 172

[56] References Cited

U.S. PATENT DOCUMENTS

| | | | |
|---|---|---|---|
| 3,062,612 | 11/1962 | Boucher | 252/395 |
| 4,674,878 | 6/1987 | Vo Dinh | 356/301 |
| 4,781,458 | 11/1988 | Angel et al. | 356/301 |
| 4,802,761 | 2/1989 | Bowen et al. | 356/301 |
| 5,017,007 | 5/1991 | Milne et al. | 356/301 |
| 5,255,067 | 10/1993 | Carrabba et al. | 356/301 |
| 5,327,211 | 7/1994 | Carron et al. | 356/301 |
| 5,400,136 | 3/1995 | Vo-Dinh | 356/301 |

OTHER PUBLICATIONS

"The Raman Microprobe: A New Analytical Tool", by G.J. Rosasco and E.S. Etz, Research/Development vol. 28, No. 6, Jun. 1977, pp. 20-32.

E. Roth and W. Kiefer, "Surfce-Enhanced Raman Spectroscopy as a Detection Method in Gas Chromatography," Applied Spectroscopy, vol. 48, No. 10, 1994 pp. 1193-1195.

Ken Muller and Keith Carron, "Adsorption of Chlorinated Ethylenes at 1-Octadecanethiol-Modified Silver Surfaces," Analytical Chemistry, vol. 66, No. 4, Feb. 15, 1994 (pp. 478-483).

*Primary Examiner*—Joseph W. Drodge
*Attorney, Agent, or Firm*—William E. Hein

[57] ABSTRACT

The present invention provides a generalized molecule-specific means of detection that can be applied to all existing separation systems with particular emphasis directed toward those methods based upon chromatographic, electrophoretic, and extractive techniques. The SERS method of detection of the present invention consists of the modification of SERS substrates by the application of a stabilizing coating that also reproduces or mimics the specific separation process being utilized. This ability to reproduce the specific separation process at the detector makes this method of detection universal for all types of analytes and separation methods. The detector of the present invention contains a noble metal foil, usually silver, that has been roughened to produce the SERS effect or a SERS active noble metal film that has been deposited onto a transparent substrate. A particularly unique feature of the invention is the use of stabilizing coatings with the SERS substrates. The coating is attached to the SERS substrate through chemical bonds such as thiol linkages or through physisorb polymeric coatings.

14 Claims, 3 Drawing Sheets

MOLECULAR SPECIFIC DETECTOR FOR SEPARATION SCIENCE USING SURFACE ENHANCED RAMAN SPECTROSCOPY

BACKGROUND AND SUMMARY OF THE INVENTION

This invention relates generally to the science of separating mixtures of molecular compounds or ions based on a single physical property or several unique physical properties of the mixture components and, more particularly, to a modified surface enhanced Raman scattering (SERS) detector for the structurally specific identification and quantitation of the molecular components of the mixture.

Structurally specific and structurally nonspecific detectors are known in the prior art for use in separation science applications. Two commercially available detectors of the first type employ mass spectrometry and Fourier transform infrared (FTIR) spectroscopy. Mass spectroscopy is a structural technique since the mass of the compound and the way in which the molecule fragments in the mass spectrometer can be used to infer the original structure of the molecule. Mass spectrometry is a vacuum technique particularly well suited for gas chromatography. It is also somewhat general in that it has been applied to most separation methods but requires major modifications when exchanged between methods. For example, it requires significant modification for use with liquid phase techniques because of the large expansion that occurs in going from the liquid to gas phase. FTIR is best suited for solid phase spectroscopy. FTIR is a vibrational spectroscopy and, thus, can be used to determine the structure of an analyte. Its dependence on a solid state matrix means that its use is usually off-line or at least delayed while the mobile phase matrix is evaporated. A typical FTIR separation detector consists of an infrared transparent plate or disc that is the target of a spray nozzle from the separation device. Chromatogram recording occurs while the target is slowly translated to achieve a record of the temporal separation. Reading of the chromatogram is performed either off-line or with a delay determined by the time needed to achieve solvent evaporation. Both methods can quantify the amount of material present by an absolute signal (ion current in mass spectrometry or absorption in FTIR). Since the signal depends on the molecular specie, these techniques require a standard calibration for quantitative analysis.

Many types of structurally nonspecific detection methods are known in the prior art. Examples of these include: thermal conductivty, flame ionization, and electron capture in gas chromatography; refractive index and UV absorption in liquid chromatography; and conductivity in ion chromatography. These methods inform the operator that something has passed through the separation device but provide no specific qualitative information as to what has passed. These methods may be quantitative but usually require a standard calibration curve to be so.

Raman spectroscopy is the inelastic scattering of light through energy loss into molecular vibrations. It provides a vibrational spectrum similar to that of FTIR. The selection rules for Raman spectroscopy are less severe than IR and, in general, more vibrational structure is observed in Raman spectroscopy. Raman spectra are obtained using a monochromatic light source, usually a laser, optics for collection of the scattered light, a dispersive instrument to separate the scattered light into Raman bands, and a sensitive detector. Within this general format for obtaining Raman spectra, there are many variations. The dispersive instrument may be scanned and a single detector used to obtain the spectra. More common is the use of multichannel detection, which provides a signal to noise enhancement proportional to the square root of the number of detector elements used. For example, CCD cameras are commonly used with visible and near infrared light sources. Fourier transform methods are used at longer wavelengths.

Raman spectroscopy has two distinct advantages over FTIR. It uses wavelengths that are compatible with silica based optics and detectors. This means low cost lenses, sensitive detectors, and compatibility with silica based optical fibers. The second advantage is the very weak scattering from water. Thus, it is possible to obtain Raman spectra in dilute aqueous solutions. The absence of a strong commercial presence of Raman spectroscopy is explained by two explicit disadvantages, weak signals and interference from fluorescence. The insensitivity of Raman prevents its use for trace analysis except in cases of very strong scatterers. Fluorescence is the emission of light from allowed transitions and, if present in the sample, usually increases the background to the extent that Raman cannot be observed.

In the mid 1970's, three research groups observed Raman signals from a monolayer of pyridine adsorbed to silver electrodes. One of the researchers, Richard Van Duyne at Northwestern University, observed that the signal from pyridine should be too small to observe and coined the anomalous enhancement of Raman scattering as "surface enhanced Raman scattering" (SERS). After much research, it has been determined that a majority of the SERS effect arises from an electromagnetic enhancement of optical processes near noble metal surfaces. The magnitude of the enhancement varies from metal to metal and depends on the surface preparation. Silver shows the largest enhancements of 1 to 10 million. The large enhancement made it possible to observe extremely small quantities of materials, thus overcoming the problem of Raman insensitivity.

Several years before the discovery of SERS, Kuhn et al. in Switzerland observed that the same methods that enhance Raman quench fluoescence. This phenomenon was explained as rapid energy transfer from molecular excited states into metal surfaces. The energy transfer is so efficient and rapid that the slower emission processes of fluorescence and phosphorescence do not occur. This phenomenon in combination with the large enhancements achievable with SERS set the stage for Raman spectroscopy to become a practical tool.

The missing formula for successful application of SERS to widespread problems was a method for stabilization of SERS surfaces and a method to attract molecules onto a silver surface. SERS was found to work well with only a limited class of molecules. The method for protecting the surface and generalizing the SERS effect was found by the present inventor, who observed that organic thiols reacted with silver surfaces to make very stable surface structures that could be fine tuned to create an affinity for the analyte. As a result, SERS sensors have been made for organic compounds, metal ions, pH, and CO2 with good sensitivity and selectivity.

It is a principal object of the present invention to provide a generalized molecule-specific means of detection that can be applied to all existing separation systems with particular emphasis directed toward those methods based upon chromatographic, electrophoretic, and extractive techniques.

The SERS method of detection of the present invention consists of the modification of SERS substrates by the application of a stabilizing coating that also reproduces or mimics the specific separation process being utilized. This ability to reproduce the specific separation process at the detector makes this method of detection universal for all types of analytes and separation methods.

The detector of the present invention contains a noble metal foil, usually silver, that has been roughened to produce the SERS effect or a SERS active noble metal film that has been deposited onto a transparent substrate. A particularly unique feature of this invention is the use of stabilizing coatings with the SERS substrates. The coating is attached to the SERS substrate through chemical bonds such as thiol linkages or through physisorb polymeric coatings. The coatings have multiple roles in the detection process. In addition to stabilizing the SERS substrate morphology and protecting it from chemical deterioration, the coating improves sensitivity through surface localized concentration of the analyte from the mobile phase onto the surface of the SERS substrate where detection occurs. The coating is designed to match the chemical potential of the analyte or a specific group of analytes in the mixture. The coating is thus capable of specifically attracting target analytes to the SERS surface. The SERS substrate is either exposed to the eluate stream of the separation process for on-line detection or consists of off-line detection with a spray of eluate onto a slowly moving SERS substrate. Reading of the off-line SERS-chromatogram takes place in a separate spectroscopic instrument. The substrates are easily accessible, thus making them disposable. The on-line SERS system includes a coated SERS substrate housed in a cell that couples the separation device and a spectograph through a fiber optic linkage. The spectroscopic system could consist of, for example, a fiber optic coupled laser source for Raman excitation, a fiber optic probe coupled to a spectrograph for the collection and dispersion of the Raman scattered light, and a CCD camera for the capture and display of the Raman spectrum.

DETAILED DESCRIPTION OF THE PREFERRED EMBODIMENTS

Chemical analysis of raw samples or complex mixtures begins by separation or isolation of the component or components to be analyzed. The separation is most often performed by either a chromatographic, an electrophoretic or an extractive technique. These techniques, simply classified as separation methods herein, create a temporal separation (retention) or unequal distribution of mixture components. This separation allows powerful chemical analysis methods to be applied to each component. The chemical structure of the components can be ascertained by an on-line technique capable of structural determination by timed collection of aliquots of material being separated, followed by off-line structural analysis or by a prior knowledge of the sample components and comparison of retention times with retention times of known materials. The latter is the most common method due to the lack of sensitive on-line methods for structural analysis. However, the lack of structural information places more requirements on the separation process since only components well separated from others can be analyzed. In terms of time per evaluation, the on-line technique is much superior to off-line analysis or repeated calibration of the instrument with known samples. While the on-line approach is the obvious choice, it is limited by the currently available detector technology. The present invention replaces conventional detectors and their problems with a single unit that is capable of sensitive detection and on-line structural determination for all separation methods.

Figure 1C:
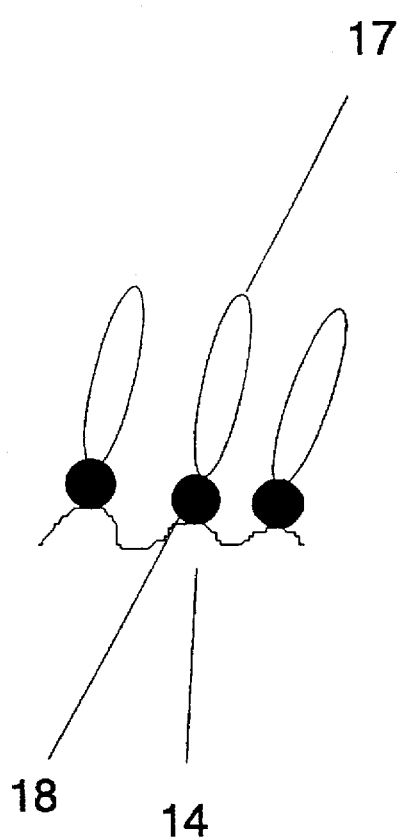
FIG. 1C is an enlarged diagram of the surface of the transparent SERS substrate of FIG. 1B.
Figure 1A:
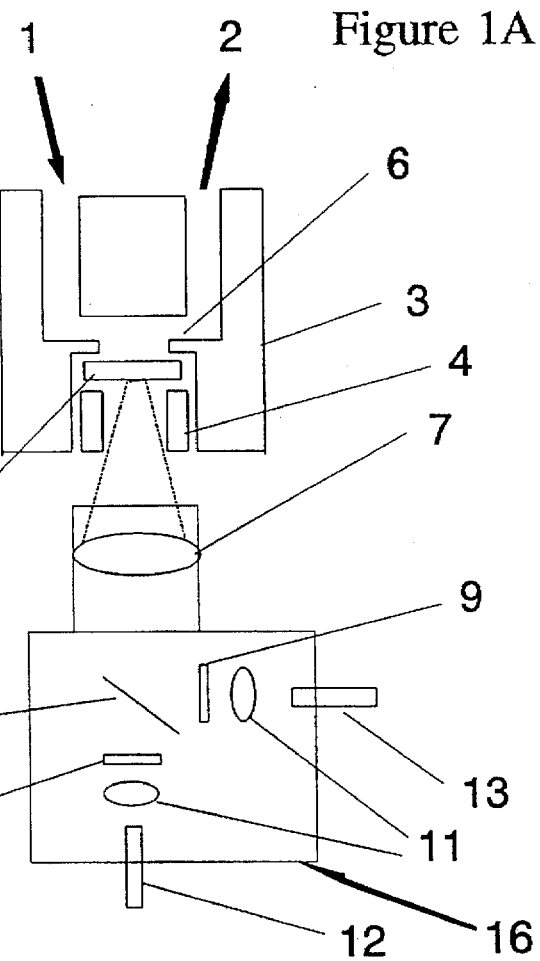
FIG. 1A is a diagram illustrating a SERS separation cell with a fiber optic coupling system, constructed in accordance with the present invention.

Referring now to FIG. 1A, there is shown a SERS separation cell 3 with a fiber optic coupling assembly 16. The cell 3 is composed of a block of material containing an input channel 1 for inflow from an external separation device and an output channel 2. A transparent coated SERS substrate 5 is held in place with a retaining ring 4 against a cell retainer 6. Optical excitation and emission are controlled by means of the fiber optic coupling assembly 16. Raman excitation is provided by an external laser source that is coupled to the transparent coated SERS substrate 5 by means of an optical fiber 12. The Raman scattered light is collected by a lens 7, which also focusses the laser light. A dichroic beamsplitter 8 passes the laser light with high efficiency and reflects the longer wavelength Raman light with equally high efficiency. Purification of the laser light and removal of the laser frequency from the Raman light is achieved with two filters 9, 10. Filter 9 is a bandpass filter, and filter 10 is a long pass filter. Two lenses 11 are used to collimate the laser light for passage through the angle dependent filter and beamsplitter elements and to focus the Raman light onto an optical fiber 13.

Figure 1B:
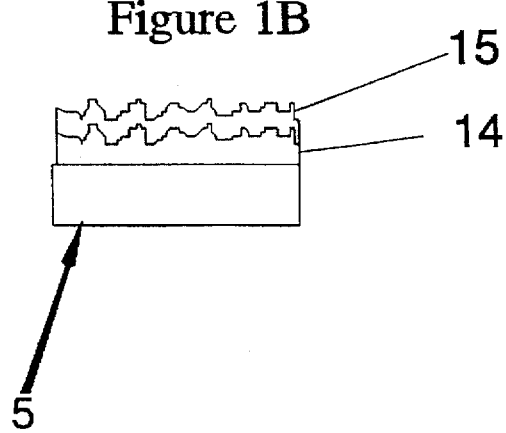
FIG. 1B is an enlarged diagram of a transparent SERS substrate employed in the separation cell of FIG. 1A.

As illustrated in FIG. 1B, the transparent coated SERS substrate 5 is composed of a transparent roughened material like silica, a thin silver coating 14, and a chemically anchored (stabilizing) affinity coating 15. For this cell, the Raman excitation and collection are performed through the back or uncoated surface of the substrate 5. This configuration maximizes mobile phase isolation, which is used to minimize Raman scattering from mobile phase components.

As illustrated in FIG. 1C, the modified SERS substrate consists of a roughened silver surface 14, an organic modifier composed of an anchor 18, and a head group 17. The roughened silver surface 14 serves to enhance the Raman scattering through the SERS effect. The anchor 18 serves to stabilize the silver morphology and to prevent oxidation of the silver surface. The head group 17 is employed to emulate the separation retention mechanism that takes place during a separation process and to thereby locally increase analyte concentration at the surface.

Figure 2:
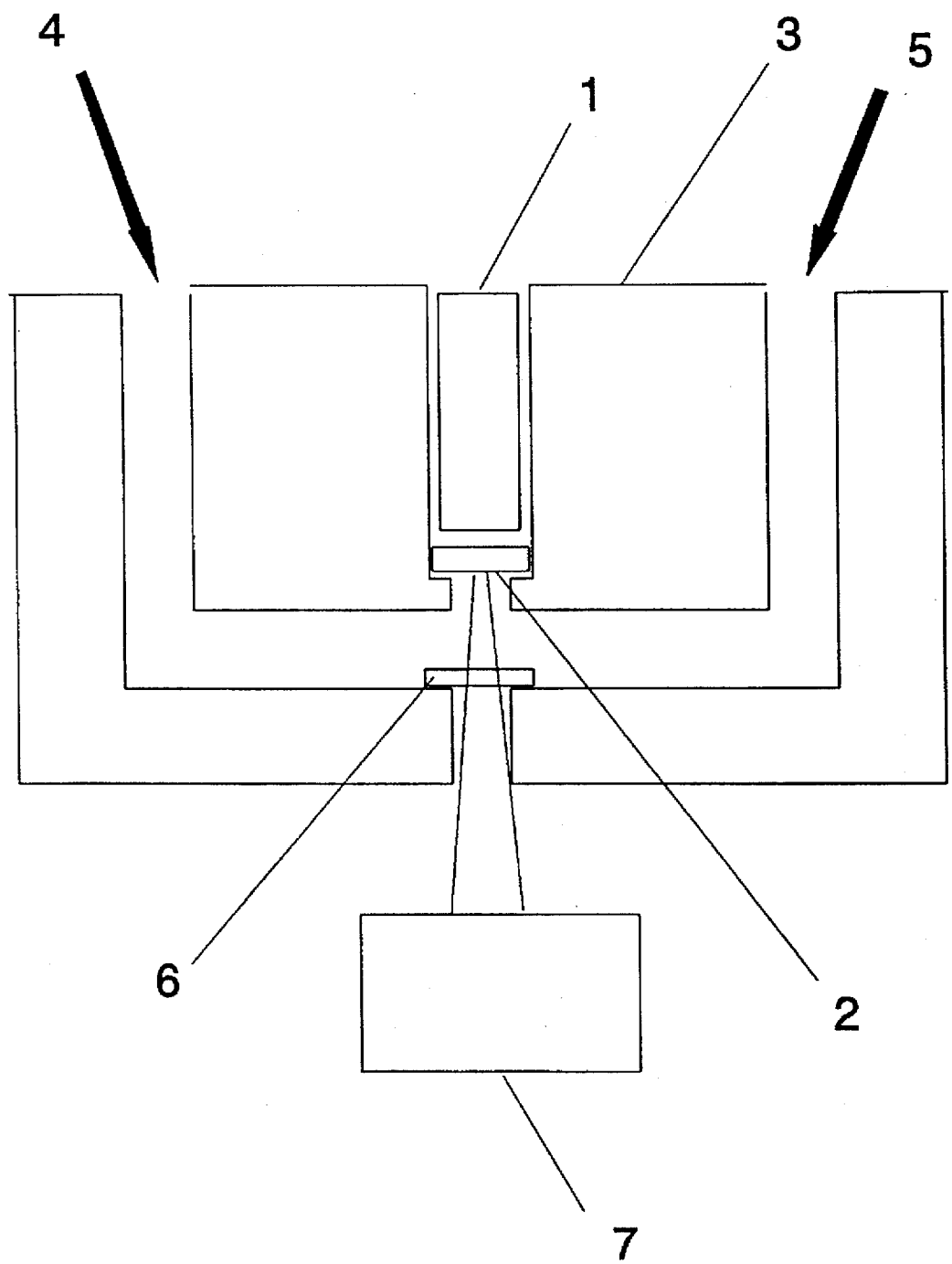
FIG. 2 is a diagram illustrating an SERS separation cell for use with opaque SERS substrates.

Referring now to FIG. 2, there is shown a cell 3 for use with opaque coated SERS substrates. Cell 3 includes an inlet 4 and an outlet 5 to allow the separation mixture to pass through the cell. A coated SERS substrate 2 is held in place by a retaining ring 1. Light from an external source for Raman excitation and collection is coupled into the cell 3 through a window 6. A fiber optic coupling assembly 7 is constructed like fiber optic coupling assembly 17 of FIG. 1C.

The present invention has been employed in the detection of a separation from a gas chromatograph. Benzene, toluene, ehtylbenzene, o-xylene, m-xylene, and p-xylene (BTEX) were detected using a modified SERS substrate. In this demonstration a SERS substrate was roughened with 30% nitric acid and was emersed in an ethanolic propanethiol solution to create a propanethiolate coating. This coating was found to prevent oxidation and to stabilize the surface allowing the substrate to be used repeatedly for several days. If the surface was not coated it was found that the SERS effect began to decrease immediately. The propanethiol coating also created an affinity for hydrophobic molecules, like the BTEX family of compounds. The affinity can be described as an emulation of the separation process that occurs on the hydrophobic coating of the chromatographic column.

Figure 3:
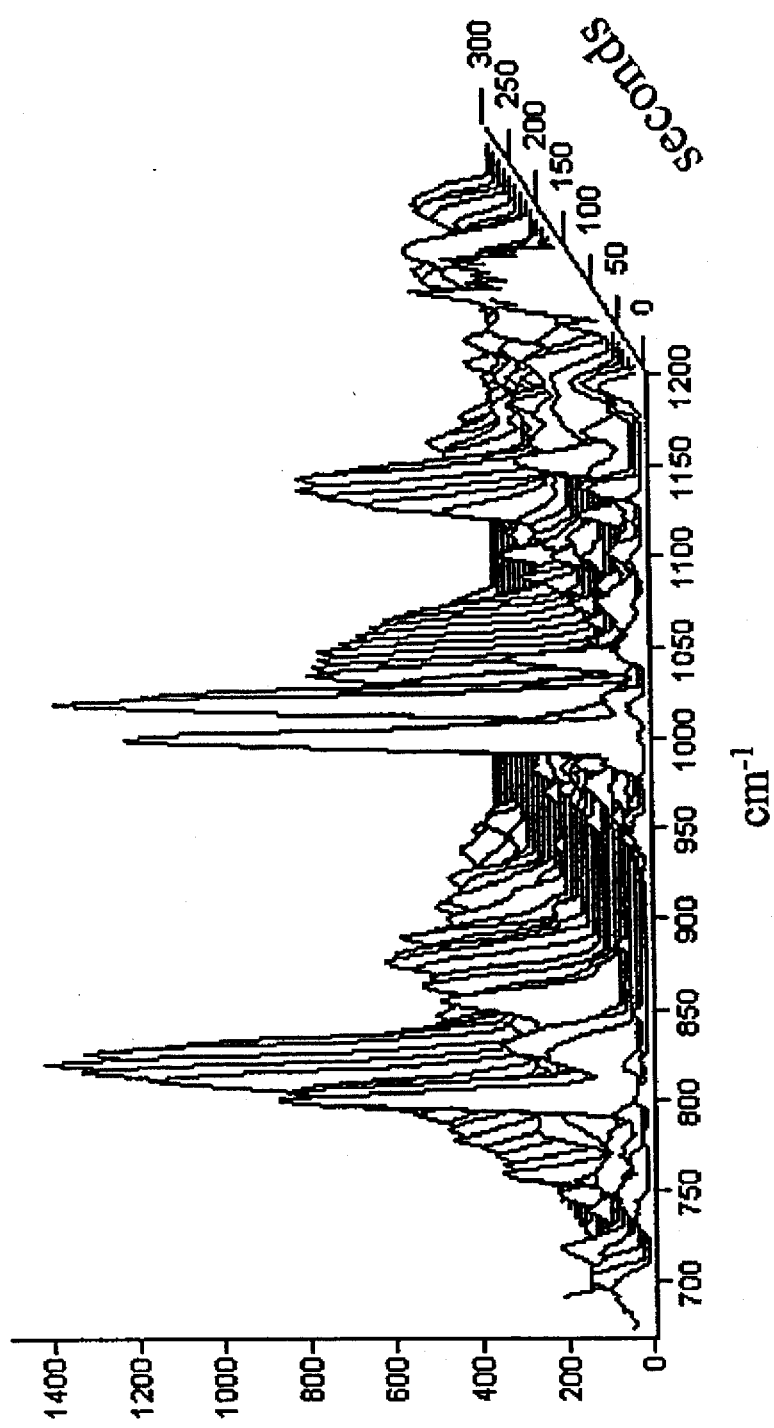
FIG. 3 is a SERS chromatogram produced using the SERS detector of the present invention.

This demonstration confirmed that the BTEX component can be detected at the nanogram level and identified through characteristic Raman features. The spectra can be quantified through the use of the internal standard peaks of the propanethiolate spectrum. The SERS detection and identification of BTEX was found to be superior to conventional thermal conductivity detection in that chromatrographic peaks that could not be time resolved by the gas chromatograph could be resolved spectrally with SERS detection. Furthermore, while the thermal conductivity detector produced a chromatogram, it did not identify the chemical constituents of the peaks coming off the column. The SERS chromatogram, illustrated in FIG. 3, provided identification of each peak.

I claim:

1. A process downstream of a chemical separation system for detecting molecules and ions in gases, liquids, and solids using a coated surface enhanced Raman scattering (SERS) substrate, the process comprising the steps of:

fabricating a SERS active metal substrate;

applying a coating to the SERS active metal substrate, the coating being formulated to prevent chemical deterioration, including oxidation, of said SERS active metal substrate, said coating comprising an organosulfur compound that forms an anchored passivating layer to the SERS active metal substrate and an organic portion characterized in creating an affinity for molecules and ions and providing internal reference for quantitative analysis of an identification of said molecules and ions; and identifying molecules and ions after separation by the chemical separation system.

2. A process as in claim 1 wherein the coating is formulated to have an affinity for specific molecules and ions to concentrate said specific molecules and ions at a surface of the coated SERS active metal substrate.

3. A process as in claim 1 wherein the coating is formulated to exhibit selectivity for a substance selected from the group consisting of a single molecule, a single ion, a class of molecules, and a class of ions.

4. A process as in claim 1 wherein the coating is formulated to exhibit an internal Raman spectrum intensity calibration standard for spectral quantitation of adsorbed, absorbed, and chemisorbed molecules and ions.

5. A process as in claim 1 wherein the coating is formulated to exhibit an internal Raman spectrum frequency calibration standard for spectral identification of adsorbed, absorbed, and chemisorbed molecules and ions.

6. A process as in claim 1 wherein the coating is formulated to emulate a coating employed within the chemical separation system.

7. A process as in claim 1 wherein the coating is formulated to stabilize a surface morphology of the SERS active metal substrate.

8. A process as in claim 1 wherein said SERS active metal substrate is selected from the group of SERS active metals consisting of silver, copper, gold, platinum, gallium, and indium.

9. A process as in claim 8 wherein the step of fabricating the SERS active metal substrate includes roughening the SERS active metal substrate by chemical etching.

10. A process as in claim 8 wherein the step of fabricating the SERS active metal substrate includes vapor deposition of at least one discontinuous metal film.

11. A process as in claim 8 wherein the step of fabricating the SERS active metal substrate comprises vapor depositing the selected SERS active metal onto a preroughened substrate.

12. A process as in claim 8 wherein the step of fabricating the SERS active metal substrate includes roughening the SERS active metal substrate by an electrochemical method.

13. Apparatus for performing surface enhanced Raman scattering (SERS) spectroscopy of a coated SERS active metal substrate downstream of a chemical separation system to detect molecules and ions in gases, liquids, and solids, the apparatus comprising:

a laser for producing monochromatic excitation;

a SERS active metal substrate coated with a coating formulated to prevent chemical deterioration, including oxidation, of said SERS active metal substrate, said coating comprising an organosulfur compound that forms an anchored passivating layer to the SERS active metal substrate and an organic portion characterized in creating an affinity for molecules and ions and providing internal reference for quantitative analysis of an identification of said molecules and ions;

a fiber optic coupler for transmitting the monochromatic excitation produced by said laser to the SERS active metal substrate and for collecting a SERS signal received from the SERS active metal substrate;

a spectrometer connected to the fiber optic coupler for receiving the collected SERS signal, for dispersing the collected signal into a Raman spectrum, and for detecting the Raman spectrum to produce an electronic signal related to an intensity of the collected Raman spectrum.

14. Apparatus as in claim 13 wherein said SERS active metal substrate is optically transparent to provide isolation of the molecules and ions transmitted from the fiber optic coupler.

* * * * *